US007959576B2

(12) United States Patent
Torpo et al.

(10) Patent No.: US 7,959,576 B2
(45) Date of Patent: Jun. 14, 2011

(54) APPARATUS FOR DETECTING DIASTOLIC HEART FAILURE

(75) Inventors: Maria Torpo, Sundbyberg (SE); Malin Öhlander, Stockholm (SE); Anders Björling, Järfälla (SE); Karin Ljungström, Hässelby (SE)

(73) Assignee: St. Jude Medical AB, Jarfalla (SE)

( * ) Notice: Subject to any disclaimer, the term of this patent is extended or adjusted under 35 U.S.C. 154(b) by 593 days.

(21) Appl. No.: 10/562,302

(22) PCT Filed: May 6, 2004

(86) PCT No.: PCT/SE2004/000698
§ 371 (c)(1),
(2), (4) Date: Dec. 22, 2005

(87) PCT Pub. No.: WO2005/107582
PCT Pub. Date: Nov. 17, 2005

(65) Prior Publication Data
US 2007/0100249 A1 May 3, 2007

(51) Int. Cl.
A61B 5/021 (2006.01)
(52) U.S. Cl. ........................................ 600/526; 600/513
(58) Field of Classification Search .................. 600/508, 600/526, 513; 607/6, 9, 17, 18, 23, 25, 28
See application file for complete search history.

(56) References Cited

U.S. PATENT DOCUMENTS

| 5,334,222 | A | * | 8/1994 | Salo et al. | 607/17 |
| 5,584,868 | A | * | 12/1996 | Salo et al. | 607/17 |
| 5,800,471 | A | * | 9/1998 | Baumann | 607/25 |
| 5,814,088 | A | * | 9/1998 | Paul et al. | 607/28 |
| 6,314,322 | B1 | * | 11/2001 | Rosenberg | 607/17 |
| 6,751,504 | B2 | * | 6/2004 | Fishler | 607/25 |
| 6,876,881 | B2 | * | 4/2005 | Baumann et al. | 607/18 |
| 6,915,162 | B2 | * | 7/2005 | Noren et al. | 607/23 |
| 6,985,772 | B2 | * | 1/2006 | Holmstrom et al. | 607/9 |
| 6,988,002 | B2 | * | 1/2006 | Kramer et al. | 607/18 |
| 7,022,077 | B2 | * | 4/2006 | Mourad et al. | 600/449 |

(Continued)

FOREIGN PATENT DOCUMENTS

| WO | WO 02/43587 | 6/2002 |
| WO | WO 02/053026 | 7/2002 |
| WO | WO 2005/107582 | * 11/2005 |

OTHER PUBLICATIONS

"New Concepts in Diastolic Dysfunction and Diastolic Heart Failure: Part I, Diagnosis, Prognosis, and Measurements of Diastolic Function," Zile et al, Circulation, vol. 105 (2002), pp. 1387-1393.

(Continued)

Primary Examiner — Carl H Layno
Assistant Examiner — Luther G Behringer
(74) Attorney, Agent, or Firm — Schiff Hardin LLP

(57) ABSTRACT

An implantable medical apparatus for detecting diastolic heart failure, DHF, has a DHF determining device for determining at least one DHF parameter for detecting a DHF state of the heart of a patient. The DHF includes circuitry for determining, as the DHF parameter, the time duration of a predetermined phase of diastole. A pacemaker has such an apparatus and a control unit that optimizes pacing therapy and pacemaker settings depending on the determined time duration. A corresponding method of detecting diastolic heart failure, DHF, includes determining at least one DHF parameter for detecting a DHF state of the heart of a patient. As the DHF parameter, the time duration of a predetermined phase of diastole is determined.

37 Claims, 4 Drawing Sheets

U.S. PATENT DOCUMENTS

| | | | |
|---|---|---|---|
| 7,231,248 B2 * | 6/2007 | Kramer et al. | 607/9 |
| 7,239,914 B2 * | 7/2007 | Lovett et al. | 607/17 |
| 7,310,554 B2 * | 12/2007 | Kramer et al. | 607/9 |
| 7,363,077 B1 * | 4/2008 | Min et al. | 607/9 |
| 2002/0151938 A1 * | 10/2002 | Corbucci | 607/25 |
| 2005/0102002 A1 * | 5/2005 | Salo et al. | 607/17 |

OTHER PUBLICATIONS

"Diastolic Heart Failure," Mandinov et al, Cardiovascular Research, vol. 45 (2000), pp. 813-825.

"Mechanisms, Diagnosis, and Treatment of Diastolic Heart Failure," Lenihan et al, Am. Heart J., vol. 130 (1995) pp. 153-166.

* cited by examiner

APPARATUS FOR DETECTING DIASTOLIC HEART FAILURE

BACKGROUND OF THE INVENTION

1. Field of the Invention

The present invention relates to an implantable medical apparatus for detecting diastolic heart failure, DHF, of the type having a DHF determining device for determining at least one DHF parameter for detecting a DHF state of the heart of a patient. The invention also relates to a pacemaker having such an apparatus, and a method for detecting diastolic heart failure, DHF, including the step of determining at least one DHF parameter for detecting a DHF state.

2. Description of the Prior Art

There is a growing recognition that congestive heart failure caused by a predominant abnormality in the diastolic function, i.e. diastolic heart failure, DHF, is both common and causes significant morbidity and mortality. Therefore early detection of DHF is important such that a suitable treatment can be started. Patients do not, however, seem to have symptoms at an early stage. In addition it has been hard to separate diastolic and systolic heart failure and they may also exist simultaneously.

The time progress of different phases of diastole of a patient suffering from DHF is changed vis-à-vis that of a healthy person, see Michael R. Zile and Dirk L. Brusaert, "New Concepts in Diastolic Dysfunction and Diastolic Heart Failure: Part I", Circulation 2002; 105: 1387. Thus DHF can be divided into three phases, see FIG. 1. FIG. 1a shows left atrial pressure, LA dotted line, and left ventricular pressure, LV solid line, as functions of time for a normal, healthy state and for three phases of DHF. The first phase of DHF is referred to as "Impaired Relaxation". In this phase characteristic times related to relaxation and filling of the left ventricle is prolonged compared to corresponding times of a normal heart. After this phase the disease progresses into a phase called "Pseudonormal". In this phase the heart compensates and the characteristic times returns to more normal values, close to those of the normal heart. This phase is followed by the final phase of DHF called "Restrictive". In the final phase the characteristic times are shorter than for the normal heart. FIG. 1b shows corresponding measured mitral blood flow velocities. Letter "E" denotes the so-called E-wave, early filling of the ventricle, and "A" the A-wave, contribution from the atrium during its contraction.

SUMMARY OF THE INVENTION

An object of the present invention is to utilize these changes in time during diastole of patients suffering from DHF for proposing a technique for DHF detection.

The above object is achieved in accordance with the present invention by an implantable medical apparatus for detecting DHF, including a sensor that interacts with a heart to obtain information associated with functioning of the heart, and a DHF determining device supplied with the sensed information that detects a DHF state of the heart from the sensed information by determining, as a DHF parameter, a time duration of a predetermined phase of diastole of the heart.

Thus with the present invention early detection of DHF is possible and it is also possible to detect how the disease progresses. Even the beginning of a DHF of a healthy person can be detected.

In embodiments of the apparatus according to the invention the DHF determining device includes a sensor and a calculating unit for determining the time, DT, from the occurrence of peak blood flow velocity through the mitral valve to zero blood flow velocity therethrough as said DHF parameter. The sensor and calculating unit are adapted to determine DT by extrapolating the mitral blood flow velocity to zero, if zero velocity is not obtained before atrial contraction. The sensor and calculating unit are then preferably adapted to determine the time derivative of the blood flow velocity through the mitral valve shortly after said peak blood flow velocity for use for linearly extrapolating the blood flow velocity to zero. DT denotes the E-wave deceleration time or "Dec time" related to the early filling of the left ventricle as mentioned above. If zero velocity is not obtained due to the atrial contraction, so-called A-wave influence, which will be described more in detail below. DT can consequently be determined by extrapolation in such situations.

In another embodiment of the apparatus according to the invention the DHF determining device includes a sensor and a calculating unit for determining isovolumic relaxation time, IVRT, i.e. the time from the closing of the aortic valve to the opening of the mitralis valve, as the DHF parameter.

In other embodiments of the apparatus according to the invention the sensor and calculating unit detect an IEGM or an impedance in the patient's heart or detect sound or activity in which case the sensor is an accelerometer. The sensor is intended to be placed on the left ventricle of the patient's heart, for determining DT and/or IVRT. Thus e.g. IVRT can be determined from impedance measurements between the left and right ventricles, or possibly between the left ventricle and right atrium. Since there is no change in the blood volume between electrodes located as indicated above during IVRT, the impedance will be substantially constant. IVRT can consequently be identified as a "still" period in the impedance after systole. IVRT can also be determined by an accelerometer positioned on the left ventricle, for instance in one of the coronary veins running on the outside of the left ventricle. IVRT is then determined by the time the ventricle is still after systole, since the ventricle is still during IVRT. No blood enters or leaves the ventricle during this phase of the cardiac cycle, only a redistribution of the pressure takes place within the ventricle without change of volume of the ventricle. DT can be determined by e.g. listening to the blood flow through the mitral valve. The blood velocity is correlated to the frequency of the heart sound signal, its derivative corresponds to the acceleration of the blood, and DT is calculated therefrom.

In other embodiments of the apparatus according to the invention the DHF determining device determines the time duration at predetermined time intervals and a memory is provided for storing the determined time durations. The DHF determining device alternatively can be adapted to determine changes in the time duration and a memory is provided for storing the determined changes in time duration. During the follow-up of the patient stored parameters are downloaded from the memory and are evaluated by the physician for studying the progression of the disease It is also possible to provide an alerting means that is triggered if deviations of the determined time duration from predetermined limit values exceed a predetermined threshold value, or a change in the determined time duration exceeds a predetermined threshold value. Thus in response to the detection of a change in the DHF parameter indicating that the patient is developing DHF or the patient is progressing into a new phase of DHF an alert can be sent calling for a follow-up by a physician.

The invention also relates to a pacemaker provided with the apparatus for detecting DHF and a control unit that optimizes pacing therapy and pacemaker settings depending on the determined time duration, as well as a method of detecting DHF.

DESCRIPTION OF THE PREFERRED EMBODIMENTS

Figure 1A:
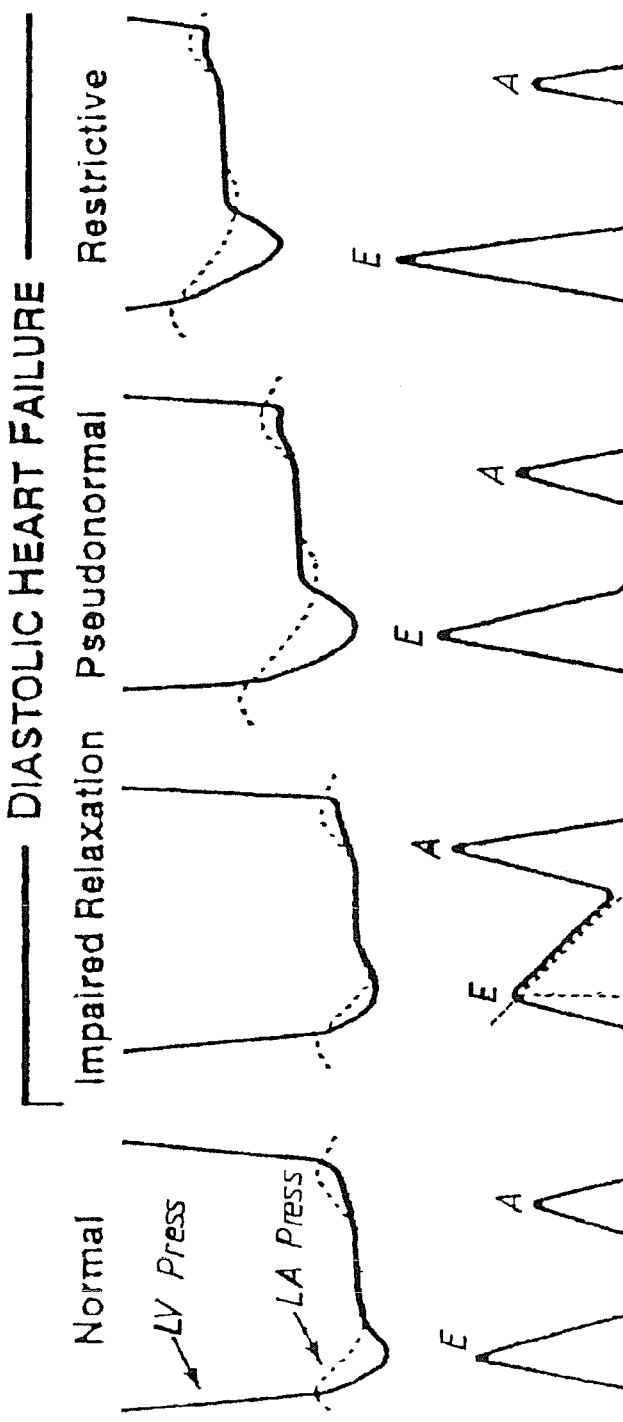
FIGS. 1a and 1b respectively show left ventricular and left atrial pressures and mitral blood flow velocity for a normal heart and for three phases of DHF.
Figure 1B:
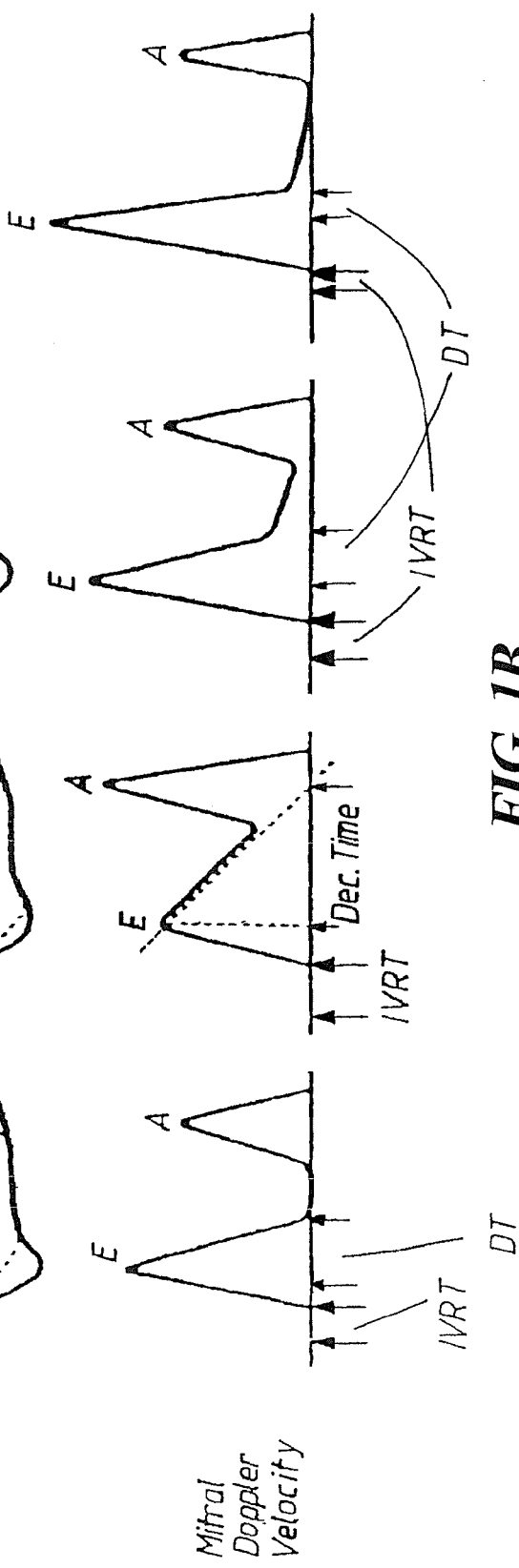

FIG. 1a shows left ventricular pressure, LV Press solid line, and left atrial pressure, LA Press dotted line, during diastole and FIG. 1b corresponding mitral Doppler left ventricular blood inflow, as measured by echocardiography, for a normal healthy heart and for three phases of diastole. Normal diastolic function is characterized by a predominant early diastolic mitral flow, E-wave, exceeding the velocity of left ventricular filling contributed by atrial contraction, A-wave in the figure. With impaired relaxation atrial contraction contributes relatively more to ventricular filling, viz. A-wave>E-wave, with prolonged deceleration of the E-wave, usually >240 msec. This phase of DHF "Impaired Relaxation" is common with increasing age and may identify patients at risk for DHF. When ventricular diastolic pressure increases to the point where atrial contraction contributes little to the filling, the E-wave again becomes predominant but with rapid deceleration, first in a "Pseudonormal" pattern and ultimately in a "Restrictive" pattern, characterized by a high E-wave velocity of usually more than twice the A-wave velocity.

One of the time durations which can be used to indicate the progress of DHF is the E-wave deceleration time, DT "Dec. Time", see FIG. 1b. DT is defined as the time length from the point of blood peak velocity through the mitral valve to the point of zero velocity, cf. FIG. 1b. If zero velocity is not reached due to the A-wave influence, DT is calculated by extrapolation as illustrated in FIG. 1b for the phase "Impaired Relaxation". The time derivative of the flow velocity through the mitral valve shortly after the blood flow peak velocity is determined for use for linearly extrapolating the blood flow velocity to zero. By measuring DT the beginning of a DHF and its progress can be detected.

The progress of DHF can be divided into three phases as mentioned above and each of these phases causes a change in DT, see FIG. 1b. The first phase of DHF is referred to as "Impaired Relaxation". During this phase DT is much longer than in a normal heart. After this phase the disease progresses into a phase called "Pseudonormal". In this phase the heart compensates and DT returns to more normal values, close to the DT value of a normal heart. This phase is followed by the final stage of DHF called "Restrictive". In this phase DT is shorter than DT of a normal healthy heart.

Another time duration that can be used to indicate the progress of DHF is the isovolumic relaxation time, IVRT, as mentioned above. In the "Impaired Relaxation" phase of diastole IVRT is longer than for a healthy heart, as appears from FIG. 1b. In the "Pseudonormal" phase the heart is compensating and IVRT returns to more normal values. In the final "Restrictive" phase IVRT is decreased to a shorter value than IVRT of the normal heart, cf. FIG. 1b.

A pacemaker according to the invention will preferably use its sensors for determining IEGMs or impedance measurements for measuring and calculating DT or IVRT at given time intervals, as will be described in further details below, and either store DT or IVRT or changes in DT or IVRT in the memory of the pacemaker. In the follow-up the development of DT or IVRT over time is downloaded from the pacemaker and the physician can evaluate the results and study the progression or regression of the disease.

An alerting unit can also be provided to send an alert, calling for a follow-up for the patient in question, in response to the detection of a change in DT or IVRT indicating that the patient is developing DHF or the patient is progressing into a new phase of DHF.

Figure 2:
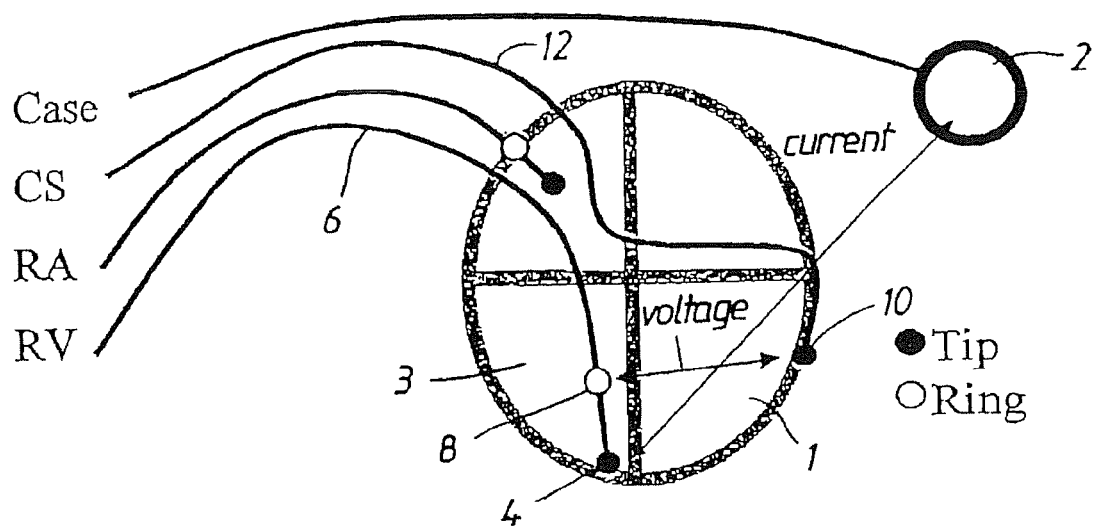
FIGS. 2, 3 and 4 respectively illustrate impedance measurements for determining IVRT in three embodiments according to the invention.

IVRT is initiated by the closing of the aortic valve and terminated by the opening of the mitral valve. To determine when the aortic and mitral valves closes 3 and opens respectively impedance measurements or some kind of sensor can be used. FIG. 2 illustrates an example of impedance measurements between left and right ventricles 1, 3. A current is supplied between the pacemaker case, schematically shown at 2, and the tip electrode 4 of a right ventricular lead 6, and the resulting voltage is measured between the ring electrode 8 of the ventricular lead 6 and the tip electrode 10 of a unipolar coronary sinus lead 12.

Figure 3:
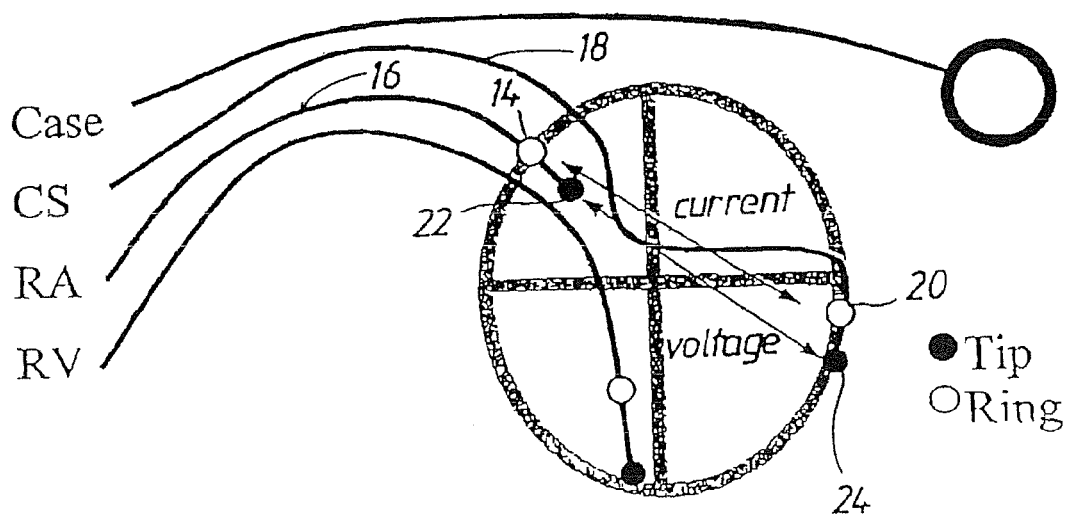

FIG. 3 illustrates an example wherein current is fed between the ring electrode 14 of a bipolar right atrial lead 16 and the ring electrode 20 of a bipolar scoronary sinus lead 18, and the resulting voltage is measured between the tip electrodes 22 and 24 of the right atrial lead 16 and the coronary sinus lead 18 respectively.

Figure 4:
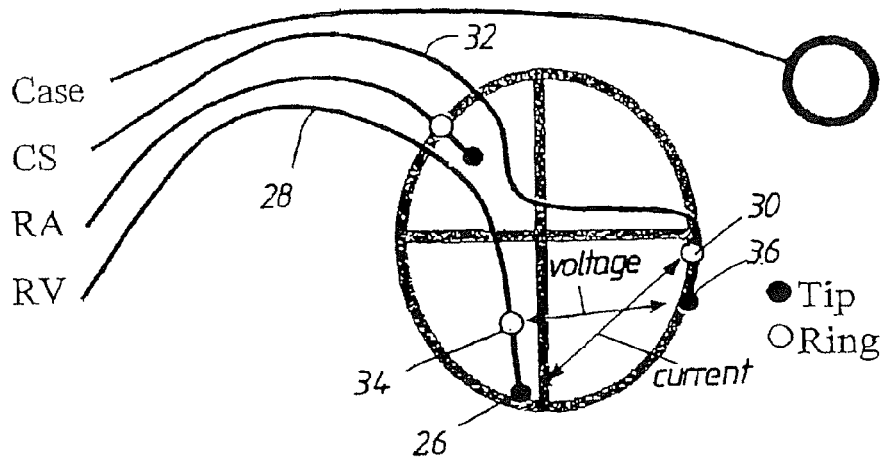

FIG. 4 illustrates still another embodiment wherein current is supplied between the tip electrode 26 of a bipolar right ventricular lead 28 and the ring electrode 30 of a bipolar coronary sinus lead 32, and the resulting voltage is measured between the ring electrode 34 of the right ventricular lead 28 and the tip electrode 36 of the coronary sinus lead 32.

Since there is practically no change in the blood volume during IVRT between the electrodes used in the embodiments illustrated above, the impedance measured in this way is substantially constant. IVRT can consequently be identified as the "still" period in the impedance after systole.

Figure 5:
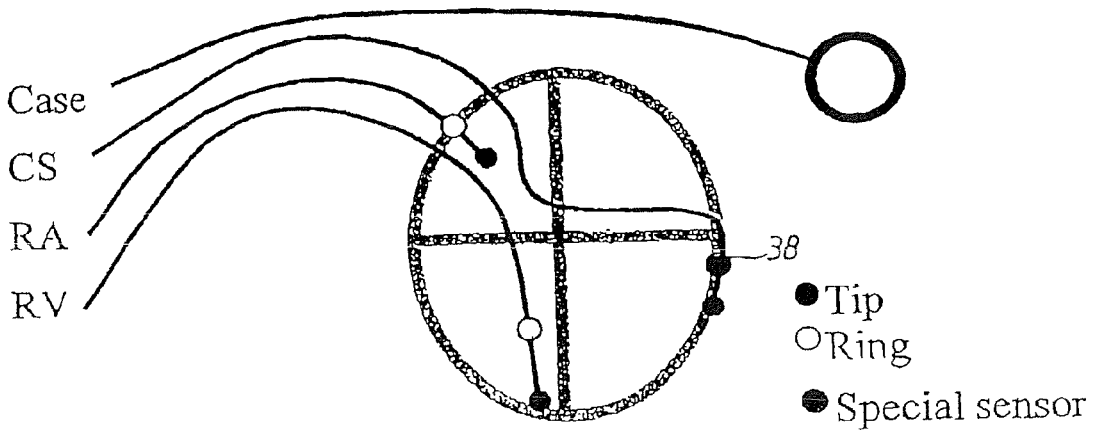
FIG. 5 illustrates an embodiment of the invention making uses of special sensors for DT and IVRT determination.

FIG. 5 illustrates an embodiment wherein a special sensor 38 is used. This sensor can be of a kind which picks up noise or registers mechanical events, such as for instance a so-called CMES-sensor, cardiac mechanical sensor. The CMES-sensor is a piezoelectric sensor the output signal of which contains a. o. pressure information. This information comprises several components, and in a certain frequency range the sensor is sensible to noise, i.e. it works as a microphone. The signal from the sensor comprises also the true pressure and its derivative. By suitable filtering of the sensor signal valve openings and closings can be detected.

The sensor 38 in FIG. 5 can alternatively be an accelerometer positioned on the left ventricle, for instance in one of the coronary veins running on the outside of the left ventricle, as shown in the figure. IVRT is then detected as the time when the ventricle is still after systole. During this time no blood leaves or enters the ventricle which consequently does not change volume.

DT can be determined in an analogous way by impedance measurements or by noise measurements with the aid of a microphone positioned in a coronary vein as illustrated in FIG. 5, or positioned in the right ventricular apex. DT can also be determined by an accelerometer positioned on the outside of the left side of the heart, i.e. in the coronary sinus.

The time duration used as parameter for detection of DHF can also be determined by more than one of the above described techniques.

Figure 6:
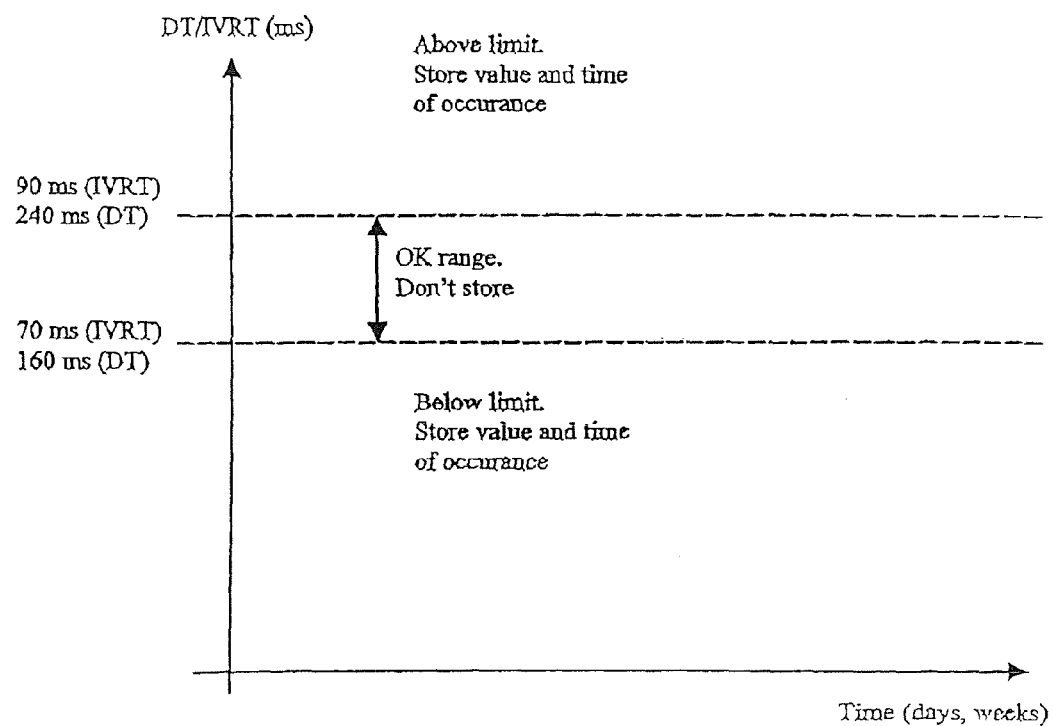
FIG. 6 is a diagram illustrating how DT and IVRT values are stored for subsequent evaluation, and the emission of a DHF alert, in accordance with an embodiment of the invention.

Typical values of IVRT of a healthy person are 70-90 msec depending on age and other parameters, and typical values of DT of a healthy person are 160-240 msec. IVRT and DT values above 90 and 240 msec respectively are assumed to characterize a state of impaired relaxation, and values below 70 and 160 msec respectively are characterizing the restrictive phase of DHF. Thus an increase or decrease of IVRT and DT above or below the above mentioned limit values are indications of DHF and should therefore call for attention. This is illustrated in FIG. 6 which shows that time duration values within the normal range are not stored, whereas time duration values above or below the prescribed limit values are stored together with their times of occurrence. These measured time duration values outside the normal range can also be triggering an alert.

The amount of deviation of the measured time lengths above or below their respective limit values is an indication of the severity of the DHF.

Thus, if the IVRT and DT values fall outside their respective normal ranges these values are stored together with the amounts by which the time lengths exceed or are below the respective limit. Possible erroneous measurement values are filtered out, such that single or very few time duration values outside the normal ranges should not result in a DHF detection, and not trigger an alert.

We claim as our invention:

1. An implantable medical apparatus for detecting diastolic heart failure (DHF) comprising:
    a sensor configured to interact with a heart to obtain information associated with functioning of the heart; and
    a DHF determining device supplied with said information that detects a DHF state of the heart from said information by extracting from said information a time duration between predetermined diastolic events in a diastolic phase of the heart representing only a portion of said diastolic phase, and determining that said DHF state exists, and emitting an output signal indicating said DHF state when said time duration exceeds an upper limit value or is below a lower limit value.

2. An apparatus as claimed in claim 1 wherein said DHF determining device comprises a comparator that compares said time duration with said upper limit value and said lower limit value to obtain a comparison result, said comparison result being indicative of said DHF state.

3. An apparatus as claimed in claim 1 wherein said DHF determining device comprises a calculating unit that calculates, from said information from said sensor, said time duration, as a time from an occurrence of peak blood flow velocity through the mitral valve of the heart to a time of occurrence of zero blood flow velocity through the mitral valve of the heart.

4. An apparatus as claimed in claim 3 wherein said calculating unit determines said time duration by extrapolating said mitral blood flow velocity to zero, if an actual occurrence of zero blood flow velocity through the mitral valve does not occur before an atrial contraction of the heart.

5. An apparatus as claimed in claim 4 wherein said calculating unit extrapolates the mitral blood flow velocity to zero by determining a time derivative of blood flow velocity through the mitral valve shortly after said occurrence of said peak blood flow velocity through the mitral valve.

6. An apparatus as claimed in claim 3 wherein said sensor senses an IEGM signal from the heart, and wherein said calculating unit calculates the time of occurrence of said peak blood flow velocity through the mitral valve to the time of occurrence of zero blood flow velocity through the mitral valve from said IEGM.

7. An apparatus as claimed in claim 3 wherein said sensor is an impedance sensor that senses an impedance of the heart, and wherein said calculating unit calculates the time from the occurrence of said peak blood flow velocity through the mitral valve to zero blood flow velocity through the mitral valve from said impedance.

8. An apparatus as claimed in claim 3 wherein said sensor is a sound sensor that detects a sound signal associated with said functioning of the heart, and wherein said calculating unit calculates the time from the occurrence of said peak blood flow velocity through the mitral valve to zero blood flow velocity through the mitral valve from said sound signal.

9. An apparatus as claimed in claim 3 wherein said sensor is an accelerometer that detects an activity signal representing activity of a subject in whom said DHF determining device is implanted, and wherein said calculating unit calculates the time from the occurrence of said peak blood flow velocity through the mitral valve to zero blood flow velocity through the mitral valve from said activity signal.

10. An apparatus as claimed in claim 3 wherein said DHF determining device determines said time duration respectively at predetermined time intervals, thereby obtaining a plurality of time durations, and comprises a memory in which said plurality of time durations are stored.

11. An apparatus as claimed in claim 3 wherein said DHF determining device determines said time duration respectively at a plurality of predetermined time intervals, and comprises a comparator that compares each of said time durations to an upper limit value to identify a first plurality of time durations above said upper limit value and respective first magnitudes of respective deviations of said first plurality of time durations from said upper limit value, and a second plurality of time durations below said lower limit value and second magnitudes of deviations of said second plurality of time durations from said lower limit value, and comprises a memory in which said first plurality of time durations, said first magnitudes, said second plurality of time durations, and said second magnitudes are stored.

12. An apparatus as claimed in claim 3 wherein said DHF determining device determines said time duration at a plurality of different times, and determines changes in the respective time durations determined at said different times, and comprises a memory in which said changes are stored.

13. An apparatus as claimed in claim 3 comprising an alerting unit that emits a humanly perceptible alert if a deviation of said time duration from either of said upper limit value or said lower limit value exceeds a predetermined threshold value.

14. An apparatus as claimed in claim 13 wherein said alerting unit triggers said alert if a length of time that said deviation exceeds said predetermined threshold value exceeds a predetermined length of time.

15. An apparatus as claimed in claim 3 wherein said DHF determining device determines said time duration at respectively different times and detects a change in said time duration detected at respectively different times, and comprises a comparator that compares said change to a predetermined threshold value, and an alerting unit that emits a humanly perceptible alert if said change exceeds said predetermined threshold value.

16. An apparatus as claimed in claim 1 wherein said DHF determining device comprises a calculating unit that calculates, as said time duration, an isovolumic relaxation time (IVRT) from said information from said sensor.

17. An apparatus as claimed in claim 16 wherein said sensor detects an IEGM from the heart, and wherein said calculating unit determines said IVRT from said IEGM.

18. An apparatus as claimed in claim 16 wherein said sensor is an impedance sensor that measures an impedance of the heart, and wherein said calculating unit calculates said IVRT from said impedance.

19. An apparatus as claimed in claim 16 wherein said sensor is a sound sensor that detects a sound signal associated with said functioning of the heart, and wherein said calculating unit calculates said IVRT from said sound signal.

20. An apparatus as claimed in claim 16 wherein said sensor is an accelerometer that detects an activity signal of a patient in whom said DHF determining device is implanted, and wherein said calculating unit calculates said IVRT from said activity signal.

21. An implantable cardiac pacemaker comprising:
a pulse generator that emits stimulation pulses;
an electrode system configured to interact with the heart of a subject to deliver said stimulation pulses to the heart in a pacing therapy regimen;
a sensor configured to interact with a heart to obtain information associated with functioning of the heart;
a DHF determining device supplied with said information that detects a DHF state of the heart from said information by extracting from said information a time duration between predetermined diastolic events in a diastolic phase of the heart representing only a portion of the diastolic phase, and determining that said DHF state exists, and emitting an output signal indicating said DHF state when said time duration exceeds an upper limit value or is below a lower limit value; and
a control unit connected to said DHF determining device and to said pulse generator, said control device being supplied with said detector output and controlling said pulse generator to modify said pacing therapy regimen dependent on said DHF parameter.

22. An implantable cardiac pacemaker as claimed in claim 21 wherein said DHF determining device determines said time duration at a plurality of different times, and determines changes in the respective time durations determined at said different times, and wherein said implantable cardiac pacemaker comprises a memory in which said changes are stored.

23. A method for detecting diastolic heart failure (DHF) comprising:
with a sensor configured to interact with a heart, obtaining information associated with functioning of the heart;
in a computerized processor, automatically electronically detecting a DHF state of the heart from said information by extracting, from said information, a time duration between predetermined diastolic events in a diastolic phase of the heart representing only a portion of the diastolic phase, and determining that said DHF state exists and emitting an output signal indicating said DHF state when said time duration exceeds an upper limit value or is below a lower limit value; and
when said DHF state is determined to exist, emitting an output signal from said processor indicating that said diastolic state exists.

24. A method as claimed in claim 23 comprising determining said DHF state by comparing said time duration with said upper limit value and said lower limit value to obtain a comparison result, said comparison result being indicative of said DHF state.

25. A method as claimed in claim 23 comprising calculating, from said information from said sensor, said time duration, as a time from an occurrence of peak blood flow velocity through the mitral valve of the heart to a time of occurrence of zero blood flow velocity through the mitral valve of the heart.

26. A method as claimed in claim 25 comprising calculating said time duration by extrapolating said mitral blood flow velocity to zero, if an actual occurrence of zero blood flow velocity through the mitral valve does not occur before an atrial contraction of the heart.

27. A method as claimed in claim 25 comprising calculating said time duration by extrapolating the blood flow velocity to zero by determining a time derivative of blood flow velocity through the mitral valve shortly after said occurrence of said peak blood flow velocity through the mitral valve.

28. A method as claimed in claim 25 comprising, with said sensor, sensing an IEGM signal from the heart, and calculating the time of occurrence of said peak blood flow velocity through the mitral valve to the time of occurrence of zero blood flow velocity through the mitral valve from said IEGM.

29. A method as claimed in claim 25 comprising, with said sensor, sensing an impedance of the heart, and calculating the time from the occurrence of said peak blood flow velocity through the mitral valve to zero blood flow velocity through the mitral valve from said impedance.

30. A method as claimed in claim 25 comprising, with said sensor, detecting a sound signal associated with said functioning of the heart, and calculating the time from the occurrence of said peak blood flow velocity through the mitral valve to zero blood flow velocity through the mitral valve from said sound signal.

31. A method as claimed in claim 25 comprising, with said sensor, detecting an activity signal representing activity of a subject in whom said sensor is implanted, and calculating the time from the occurrence of said peak blood flow velocity through the mitral valve to zero blood flow velocity through the mitral valve from said activity signal.

32. A method as claimed in claim 25 comprising calculating, as said time duration, an isovolumic relaxation time (IVRT) from said information from said sensor.

33. A method as claimed in claim 32 comprising, with said sensor, detecting an IEGM from the heart, and calculating said IVRT from said IEGM.

34. A method as claimed in claim 32 comprising, with said sensor, measuring an impedance of the heart, and wherein said calculating unit calculates said IVRT from said impedance.

35. A method as claimed in claim 32 comprising, with said sensor, detecting a sound signal associated with said functioning of the heart, and calculating said IVRT from said sound signal.

36. A method as claimed in claim 32 comprising, with said sensor, detecting an activity signal of a patient in whom said sensor is implanted, and calculating said IVRT from said activity signal.

37. A method as claimed in claim 23 comprising determining said time duration respectively at predetermined time intervals, thereby obtaining a plurality of time durations, and electronically storing said plurality of time durations in a memory.

* * * * *